United States Patent [19]

Ranford et al.

[11] 4,235,229
[45] Nov. 25, 1980

[54] ADJUSTABLE TRACHEOSTOMY TUBE ASSEMBLY

[75] Inventors: Alan B. Ranford, Des Peres; Fred E. Satchell, Chesterfield, both of Mo.

[73] Assignee: Sherwood Medical Industries Inc., St. Louis, Mo.

[21] Appl. No.: 47,824

[22] Filed: Jun. 6, 1979

[51] Int. Cl.³ .......................................... A61M 25/02
[52] U.S. Cl. .............................. 128/207.17; 128/912; 128/DIG. 26; 128/207.15
[58] Field of Search ..................... 128/200.26, 207.17, 128/207.14, 348, 349 R, 349 B, 349 BV, 350 R, 912, DIG. 9, DIG. 26

[56] References Cited

U.S. PATENT DOCUMENTS

| 953,922 | 4/1910 | Rogers | 128/207.14 |
|---|---|---|---|
| 2,586,940 | 2/1952 | Graham | 128/DIG. 26 |
| 2,820,457 | 1/1958 | Phillips | 128/207.14 |
| 3,973,569 | 8/1976 | Sheridan et al. | 128/207.17 |
| 3,987,798 | 10/1976 | McGinnis | 128/207.17 |
| 4,033,353 | 7/1977 | LaRosa | 128/207.17 |

FOREIGN PATENT DOCUMENTS

| 103777 | 2/1926 | Fed. Rep. of Germany | 128/349 R |
|---|---|---|---|
| 653436 | 5/1936 | Fed. Rep. of Germany | 128/349 R |

*Primary Examiner*—Henry J. Recla
*Attorney, Agent, or Firm*—Wegner, Stellman, McCord, Wiles & Wood

[57] ABSTRACT

A tracheostomy tube assembly (10) includes a tracheostomy tube (11) and a neck collar (14), which limits movement of the tracheostomy tube (11), but allows adjustment of the height of the tracheostomy tube (11). The collar (14) has a deformable sleeve (29) that is oversized relative to a portion of the tracheostomy tube (11) which extends therethrough. In an undeflected condition, portions (46,46) of the sleeve (29) engage the tracheostomy tube portions (43) to fix its height. When the sleeve (29) is deflected by compressing the sleeve (29) together at selected points, the engaging sleeve portions (46,46) will be deflected away from the tracheostomy tube portions (43) to permit axial movement thereof.

11 Claims, 12 Drawing Figures

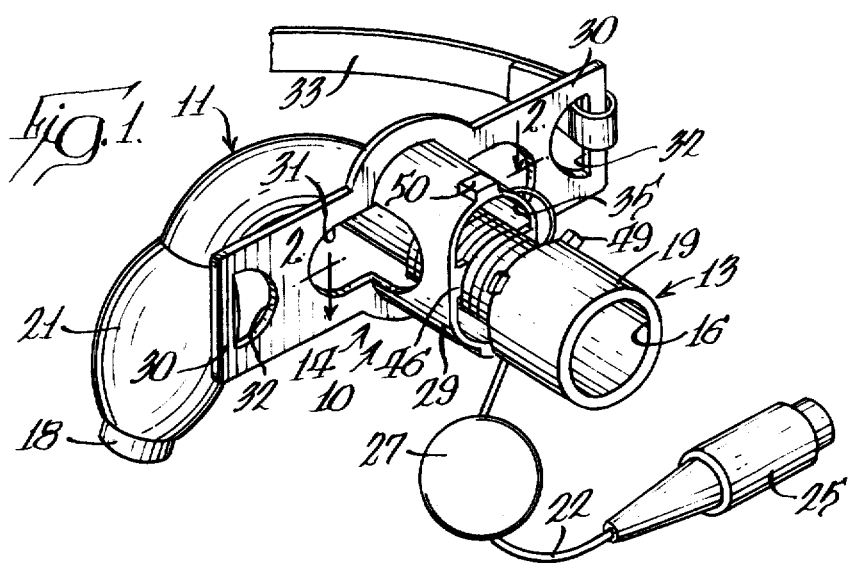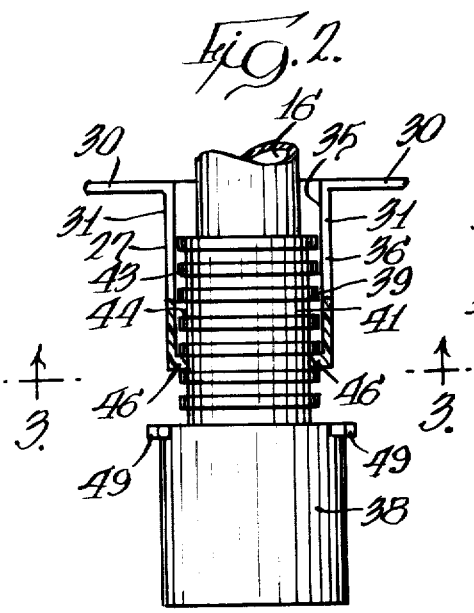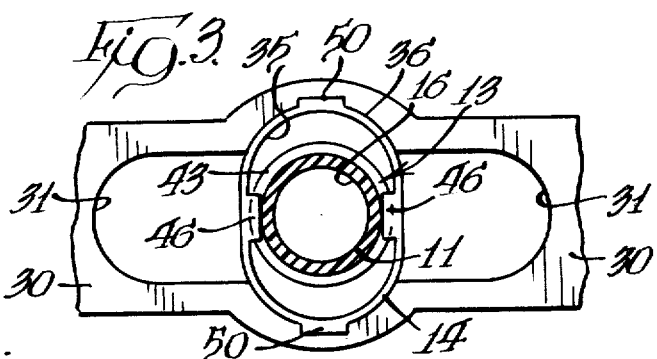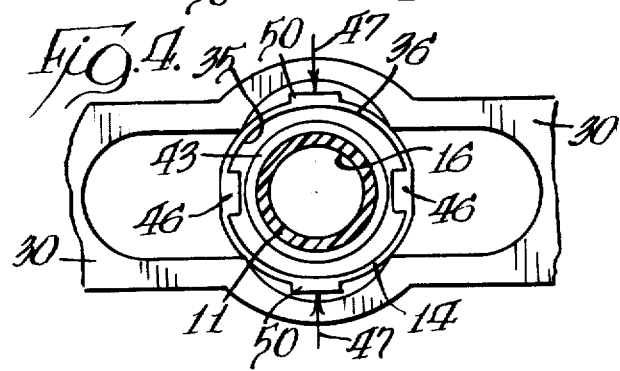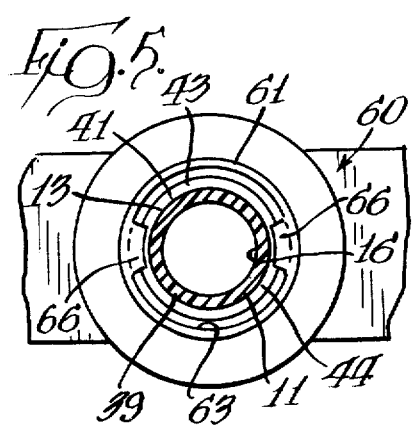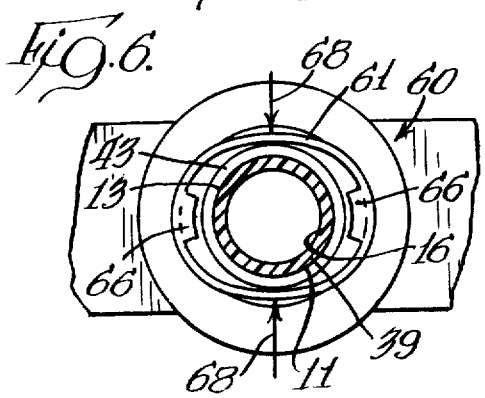

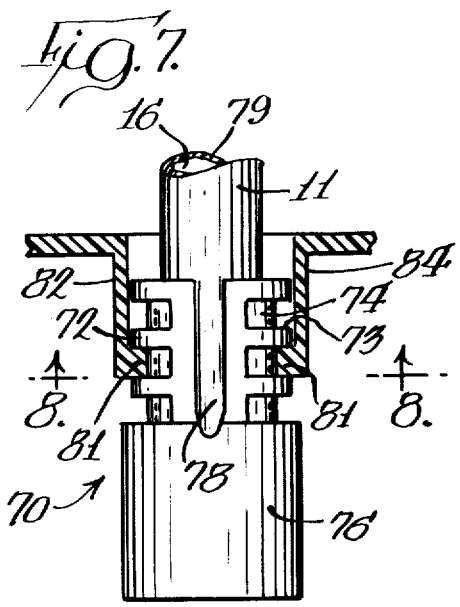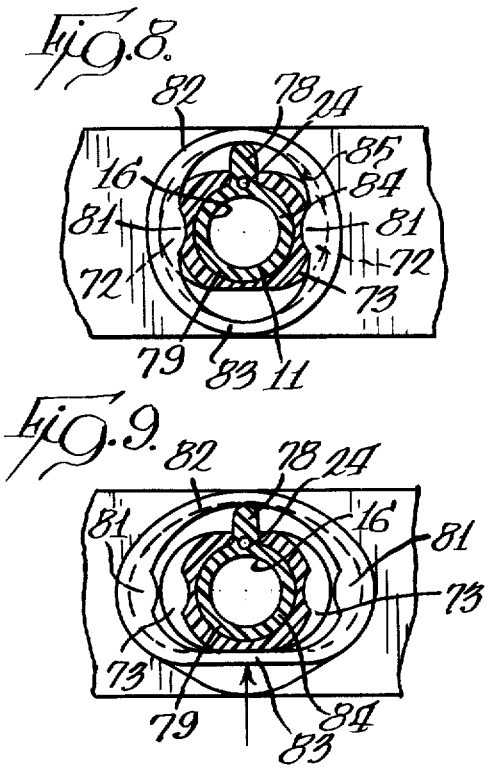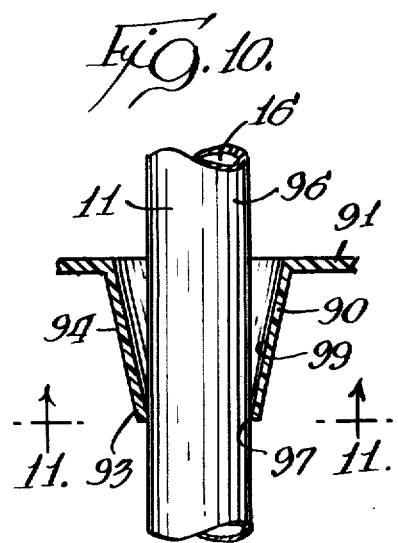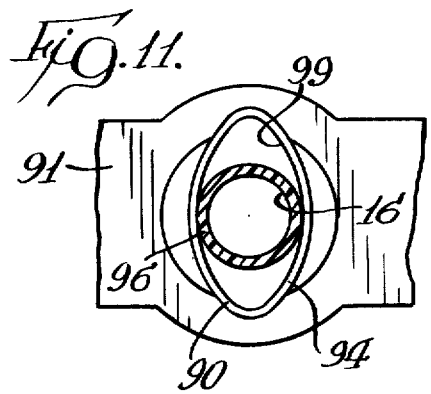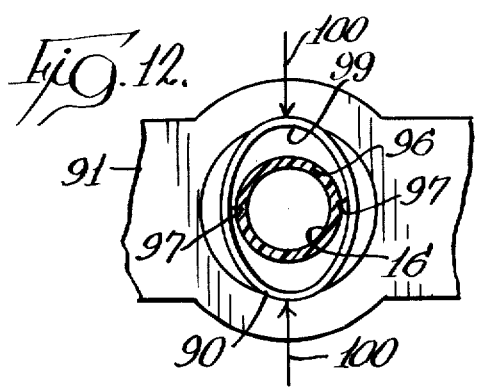

ADJUSTABLE TRACHEOSTOMY TUBE ASSEMBLY

DESCRIPTION

1. Technical Field

This invention relates generally to a tracheostomy tube assembly and, more particularly, to a tracheostomy tube assembly capable of height adjustment.

2. Background Art

A tracheostomy tube is utilized to define a clear passageway for air to the trachea. Typically, an incision is made in the front of a patient's neck and trachea, so that the tracheostomy tube can be inserted through the opening or stoma defined by the incision. When the inner or distal end of the tracheostomy tube is properly positioned, the outer or proximal end will extend from the neck a certain distance. To hold the proximal end of the tracheostomy tube in place and thereby fix the distal end in position, a collar is placed about the tube and is attached to the neck of the patient by a strap. Since the location of the incision will vary and since the size of the neck and the location of the trachea and its slope within the neck will also vary for every patient, the placement of the tracheostomy tube will necessarily vary for each patient. Consequently, the position of the collar on the tracheostomy tube must be adjusted for each patient.

Heretofore, a number of arrangements have been utilized to permit adjustment of the collar relative to the tracheostomy tube. For example, the collar and the tracheostomy tube have been constructed so that a tight fit is made therebetween or else a spring constricting ring is provided so that the tracheostomy tube is held rigidly in place. In the case of the friction fit, the tracheostomy tube was subject to slippage, while, in the case of the spring ring, the spring ring had to be released to permit adjustment. In another prior art construction, the tracheostomy tube was provided with a pair of opposed lateral tabs which were inserted into any pair of slots defined in a pair of opposed outstanding struts. In this latter device, the construction was relatively complex and expeditious adjustment was not achievable.

DISCLOSURE OF INVENTION

The present invention is directed to overcoming one or more of the problems as set forth above.

According to the invention, the neck collar defines a deformable sleeve which is inherently resilient and is oversized relative to a portion of the tracheostomy tube which extends through the sleeve. In an undeflected condition, the sleeve engages the tracheostomy tube portion to fix the relative position thereof. When selected sleeve portions are deflected inwardly by compressing the sleeve portions together, other sleeve portions engaging the tracheostomy tube portion are deflected outwardly from engagement with the tracheostomy tube portion to permit axial adjustment thereof relative to the collar. Axial adjustment is thus simply and easily made without undue pressure on or movement within the tracheal incision.

In an embodiment of the invention, the sleeve has internal lugs that engage any of an axial series of grooves or ribs formed on the exterior of the tracheostomy tube portion. Engagement between the lugs and grooves is relatively loose to permit angular motion between the collar and the tracheostomy tube on two axes so as to increase patient comfort while effectively maintaining proper height of the tracheostomy tube relative to the patient's neck.

In another embodiment, the sleeve is tapered so that the internal edge at the outward end of the sleeve pinches the tracheostomy tube portion to maintain its position.

BRIEF DESCRIPTION OF DRAWINGS

FIG. 1 is a perspective view of a first embodiment of a tracheostomy tube assembly constructed in accordance with the present invention;

FIG. 2 is a cross-sectional view of the first embodiment taken along line 2—2 of FIG. 1;

FIG. 3 is a cross-sectional view of the first embodiment taken along line 3—3 of FIG. 2;

FIG. 4 is a cross-sectional view of the embodiment of FIG. 3, but with the tubular sleeve in a deflected condition;

FIG. 5 is a cross-sectional view of a second embodiment of a tracheostomy tube assembly constructed in accordance with the present invention;

FIG. 6 is a cross-sectional view of the embodiment of FIG. 5, but with the tubular sleeve in a deflected condition;

FIG. 7 is a cross-sectional view of a third embodiment of a tracheostomy tube assembly constructed in accordance with the present invention;

FIG. 8 is a cross-sectional view of the third embodiment taken along line 8—8 of FIG. 7;

FIG. 9 is a cross-sectional view similar to FIG. 8 only with the sleeve in a deflected condition;

FIG. 10 is a cross-sectional view of a fourth embodiment of a tracheostomy tube assembly constructed in accordance with the present invention;

FIG. 11 is a cross-sectional view of the fourth embodiment taken along line 11—11 of FIG. 10; and FIG. 12 is a cross-sectional view of the embodiment of FIG. 11, but with the tubular sleeve in a deflected condition.

BEST MODE FOR CARRYING OUT THE INVENTION

Referring to the drawings, and particularly to FIG. 1, a tracheostomy tube assembly, generally designated 10, is illustrated and is broadly comprised of a curved tracheostomy tube or cannula 11, an adapter extension portion of the tracheostomy tube, generally designated 13, at the outer end of the tracheostomy tube 11, and a neck collar, generally designated 14.

The tracheostomy tube 11 and the tube extension 13 define a clear passageway 16 extending between the inner or distal end 18 of the tracheostomy tube 11 and the outer or proximal end 19 of the tube extension 13. The inner end 18 of the hollow tracheostomy tube 11 is conventional and is adapted to be inserted into a stoma cut in a patient's neck or throat (not shown) with the outer end 19 extending outwardly from the neck so as to assist the patient's respiratory ability. Fixed adjacent the inner end 18 is an inflatable endotracheal cuff 21 whose function is to provide a seal between the tracheostomy tube 11 and the patient's trachea. The cuff 21 is inflatable by means of a tube 22 which includes a passage 24 (FIG. 9) within the tracheostomy tube 11 communicating with the cuff 21. At the outer end of the tube 22 is a valve mechanism 25 which permits the introduction of air under pressure into the tube 22 for delivery to the cuff 21. Disposed along the tube 22 is an external balloon 27 which is inflated along with the cuff 21 and acts as an external indicator of the inflated condition of the cuff 21.

The flexible collar 14 limits motion of the tracheostomy tube 11 and is comprised primarily of two portions, a tubular sleeve portion 29 and elongated wind or flange portions 30 extending laterally from each side of the sleeve portion 29. Slots 32 are defined at the opposite outward ends of the flange portions 30 to enable an attachment strap or tape 33 to be looped about the flange portions 30 and secured thereto. When the collar 14 is positioned over the stoma in the patient's neck, the tape 33 is passed around the neck so as to secure the collar 14 fixedly in place. The configuration of the flange portions 30 may be varied to modify the flexibility of the collar 14 so that it can conform more readily to a particular patient's neck. The openings 31 traverse the junction between the flange portions 30 and the sleeve portion 29 to permit better visual inspection of the stoma site.

Referring to the embodiment shown in FIGS. 1 through 4, it is seen that the sleeve portion 29 extends outwardly away from the flange portions 30. Together, the sleeve portion 29 and the flange portions 30 define an opening 35 through which the tracheostomy tube 11 extends. As seen in FIG. 3, the sleeve portion wall 36 has a generally oval or elliptical cross-sectional configuration with a first, or major, axis extending vertically which is greater than a transverse second, or minor, axis which extends horizontally. The tube extension 13 of the tracheostomy tube 11 has an enlarged outward segment 38 and a reduced inward segment 39, which has a generally circular cross section. The inward segment 39 has a barrel 41 with a series of circumferential ribs 43 spaced axially thereabout to define a series of spaced circumferential grooves 44 therebetween. The opening 35 is oversized with respect to the diametrical size of the ribbed inward segment 39, i.e., the circumference of the sleeve opening 35 is greater than the circumference of the extension inward segment 39. Carried at the outward end of the sleeve portion 29 are a pair of internal lugs 46 extending radially inward along the second axis from the sleeve wall 36. The lugs 46 define an internal diameter which is smaller than the diameter of the ribs 43, when the sleeve portion 29 is undeflected. The lugs 46 engage one of the grooves 44 to hold the tube extension 13 in axial position by interacting with the adjacent ribs 43.

As indicated by arrows 47 in FIG. 4, radially-inward pressure applied at opposite sides to compress the sleeve portion 29 generally along the major axis, such as by manually pinching the sleeve portion 29 between two fingers, will cause deformation of the sleeve wall 36 to a more circular cross-sectional configuration, thereby effecting movement of the lugs 46 along the minor axis radially outward from engagement with the ribs 43. Thereafter, the tracheostomy tube extension portion 13 may be moved axially within the oversized sleeve opening 35 to adjust the position of the tracheostomy tube 11 relative to the collar 14. When the pressure is removed releasing the sleeve portion 29, the sleeve wall 36, because of its inherent resiliency, returns to its natural undeflected state or form with the internal lugs 46 engaging a groove 44 thereby locking the tracheostomy tube 11 in its new selected position.

The diameter of the sleeve portion 29 and the diametrical internal spacing between the facing portion of the lugs 46 is slightly less than the external diameter of the ribs 43 and slightly greater than the diameter of the barrel 41, respectively, so as to permit the tube extension 13 to rotate easily relative to the collar 14 as needed. The spacing between the lugs 46 could be equal to or slightly smaller than the external diameter of the barrel 41 which would produce a slight restraining force between the lugs 46 and the barrel. As seen in FIG. 3, the tube extension portion 13 may also be moved upwardly and downwardly. The tracheostomy tube assembly 10 thus allows for freedom of relative angular motion between the collar 14 and the tracheostomy tube 11 on two axes, thereby improving patient comfort.

Located on the exterior of the outward segment 38 of the tube extension 13 are radially-extending lugs 49 which may be used to suitably secure a respirator (not shown), if one is required. Oppositely-disposed external lugs 50 are provided on the exterior of the sleeve wall 36 along its major axis to facilitate the gripping of the sleeve portion 29 by the finger tips.

The collar 14 and the tracheostomy tube extension 13 may be molded from polypropylene, H.P.D.E., acetal or any other appropriate material. It is comprehended that the tracheostomy tube 11 and the tracheostomy tube extension 13 may be molded separately or integrally. If molded separately, the tube 11 and extension 13 may be connected together by any suitable means.

In the embodiment shown in FIGS. 5 and 6, the tracheostomy tube extension 13 is employed with a collar 60 in which the cross-sectional configuration of the sleeve wall 61 is approximately circular with the opening 63 defined thereby still being oversized relative to the tracheostomy tube extension 13. The internal diameter of the sleeve wall 61 is substantially greater than the external diameter of the plural ribs 43, while the diametrical spacing of the internal lugs 66 is less than the diameter of the ribs 43 and slightly greater than the diameter of the barrel 41 defining the bottom walls of the grooves 44. The spacing between the lugs 66 could be equal to or slightly smaller than the external diameter of the barrel 41 which would produce a slight restraining force between the lugs 66 and the barrel. The application or radial pressure on the sleeve wall portions inwardly along an axis perpendicular or transverse to an axial line extending between the internal lugs 66 so as to move opposed sleeve wall portions together toward the tube extension 13, as shown by arrows 68 in FIG. 6, effects radial movement of the internal lugs 66 along the aforementioned axial line outward from engagement with the ribs 43 to thereby permit axial adjustment of the relative position of the collar 60 to the tracheostomy tube. Note that the dimensional relation between the internal diameter of the sleeve wall 61 and the external diameter of the tube extension portion 13 are such that compression of the sleeve wall 61 will deflect the lugs 66 outwardly from engagement with the ribs 43 at least by the time contact of the sleeve wall 61 is made with the tube extension exterior.

In the embodiment shown in FIGS. 7 through 9, the tracheostomy tube extension 70 is constructed so as to have a generally oval or elliptical cross-sectional configuration. The barrel 71 of the tube extension 70 has a generally circular cross section, but the ribs 72 extend laterally outward from opposed sides of the barrel 71 to define grooves 73 which are lunular thereby giving the inward segment 74 a generally elliptical shape with the grooves 73 being disposed on the extended lateral sides of the tube extension 70. The outward segment 76 of the tube extension 70 is circular. In FIG. 7, a tubule 78 is seen as it extends from the wall of the tracheostomy tube 11 and passes the tube extension 70 adjacent one of the smooth constricted sides. In FIGS. 8 and 9, the passage 24, which extends parallel to the tubule 78, is seen within the wall 79 of the tracheostomy tube 11.

In the embodiment of FIGS. 7 through 9, the internal lugs 81 also have a lunular shape. When the sleeve wall 82 of the collar 84, which has an opening 85 of a generally circular cross-sectional configuration in its undeflected natural state, is deformed by pinching the sleeve portion 83 toward the tube extension 70 whereupon the internal lugs 81 will be urged laterally outward away from the ribs 72 defined on the major axis of the tube extension 70 thereby permitting axial adjustment thereof. The tubule 78 will bear against the one wall of the sleeve portion as the opposite wall 83 is deformed. The tubule 78 prevents the tube extension 70 from rotating an excessive amount, i.e. 90°, relative to the sleeve 82 whereby the ellipses will align and permit accidental relative axial movement.

In the embodiment shown in FIGS. 10 through 12, the sleeve portion 90 of the collar 91 is tapered toward its outward end 93 and the sleeve wall 94 has a cross-sectional configuration which is generally oval. The exterior of the tracheostomy tube portion 96 is cylindrical. However, the acute internal edges 97 at the outward end of the sleeve opening 99 pinch the tracheostomy tube portion 96 to frictionally hold the tracheostomy tube in selected position. If opposed sides of the sleeve portion 90 are pressed together by the application of pressure along the major axis as shown by arrows 100 in FIG. 12, then the edges 97 adjacent the sleeve opening minor axis will disengage the exterior of the tracheostomy tube portion 96 to permit relative axial adjustment thereof. Since engagement is made primarily by two contact areas, the tracheostomy tube portion 96 may swing about a line extending between those two contact areas.

We claim:

1. In a tracheostomy tube assembly (10) including a tracheostomy tube (11) having one end adapted for insertion into the trachea and the opposite end adapted to extend from the trachea through a stoma cut in a patient's throat and a collar (14,60,84,91) adapted to be fitted on the exterior of the throat and having an opening (35,63,85,99) through which the tracheostomy tube (11) passes, the improvement comprising a deformable inherently resilient sleeve (29,61,82,94) carried by said collar (14,60,84,91) and extending outwardly therefrom, a portion (39,39,74,96) of the tracheostomy tube (11) extending through said sleeve (29,61,82,94), said sleeve having an internal circumference greater than the external circumference of the portion (39,74) of the tracheostomy tube (11) extending through said sleeve, said sleeve (29,61,82,94), when said tube portion (39,74) is placed therewithin, having portions (46,66,81,97) having a width along a first axis sufficient to engage said tube portion (39,39,74,96) within said sleeve to hold the tracheostomy tube (11) at a selected height therein and having portions having a width along a second axis greater than the tube width therein, whereby the application of inward pressure (47,68,83,100) at opposite sides of the sleeve along the second axis to compress the sleeve deflects the sleeve portions (46,66,81,97) adjacent the first axis outwardly away from the tube portion (39,39,74,96) thereby permitting axial adjustment of the tracheostomy tube (11) within the collar (14,60,84,91) and whereby, upon removal of said pressure, the sleeve, due to its inherent resiliency, returns to its undeflected condition in engagement with the tube portion.

2. The tracheostomy tube assembly (10) of claim 1 wherein said tube portion (39,96) has a generally circular cross section and said sleeve portion (29,94) has a generally oval cross section when said tube portion is positioned therewithin.

3. The tracheostomy tube assembly (10) of claim 1 wherein said tube portion (39,39) defines axially-spaced external grooves (44,44) and said sleeve (29,61) has at least one internal lug (46,66) adapted to engage a selected one of said grooves (44,44).

4. The tracheostomy tube assembly (10) of claim 3 wherein said grooves (44,44) are defined between axially-spaced circumferential ribs (43,43) carried by said tube portion (39,39).

5. The tracheostomy tube assembly (10) of claim 3 wherein the internal width of said sleeve (29,61) in an undeformed condition is slightly greater than the greatest width of said tube portion (39,39) thereby permitting angular movement of said tube portion (39,39) relative to said collar (14,60).

6. The tracheostomy tube assembly (10) of claim 1 wherein said tube portion (39) has a generally circular cross section and defines axially-spaced external grooves (44) and said sleeve (61) has a generally circular cross section when said tube portion (39) is positioned within said sleeve (61), said sleeve (61) having at least one lug (66) adapted to engage said grooves (44), whereby compression of the sleeve (61) deflects the sleeve (61) to an oval cross section so as to move the lug (66) outwardly from engagement with said grooves (44).

7. The tracheostomy tube assembly (10) of claim wherein said tube portion (39) is an adapter extension (13) configured to provide an inward connection with a conventional tracheostomy tube (11) and an optional outward connection with a respirator fitting.

8. The tracheostomy tube assembly (10) of claim 1 wherein said tube portion (70) has a generally oval cross section and defines axially-spaced external grooves (73) at the opposite extended sides thereof, said sleeve (82) having a generally circular cross section and internal lugs (81) adapted to engage said grooves (73), whereby compression of the sleeve (82) effects deflection of the sleeve to an oval cross section similar to the cross section of the tube portion (70) so as to move the internal lugs (81) outwardly from engagement with the grooves (73).

9. The tracheostomy tube assembly (10) of claim 8 wherein the tracheostomy tube (11) includes an inflatable sealing cuff (21) adjacent its one end, a tubule (78) extending from said tracheostomy tube (11) and passing by said tube portion (70) adjacent one of the constricted sides of said tube portion (70) for connection to a source of air under pressure.

10. The tracheostomy tube assembly (10) of claim 1 wherein said sleeve (90) tapers toward its outward end such that the internal edges (97) of said sleeve (90) at said outward end (93) pinch said tube portion (96) when said tube portion (96) is positioned within said sleeve (90) thereby holding the tracheostomy tube (11) in place.

11. In a tracheostomy tube assembly (10) including a tracheostomy tube (11) having one end adapted for insertion into the trachea and the opposite end adapted to extend from the trachea through a stoma cut in a patient's throat and a collar (14,60,84) adapted to be fitted on the exterior of the throat and having an opening (35,63,85) through which the tracheostomy tube (11) passes, the improvement comprising a deformable sleeve (29,61,82) inherently resilient carried by said collar (14,60,84) and extending outwardly therefrom, a portion (39,39,74) of the tracheostomy tube (11) extending through said sleeve (29,61,82) and having axially-spaced external ribs (43,43,72) defining grooves (44,44,73) therebetween, said sleeve (29,61,82) having a pair of internal lugs (46,66,81) adapted to engage said grooves (44,44,73), said lugs (46,66,81) defining an internal diameter smaller than the diameter of the ribbed tube portion (39,39,74) sufficient to maintain said lugs (46,66,81) in engagement with said grooves (44,44,73) so as to hold the tracheostomy tube (11) at a selected height therein, said sleeve (29,61,82) having an internal circumference greater than the external circumference of the portion of the tracheostomy tube (11) extending through said sleeve (29,61,82), whereby the application of inward pressure (47,68,83) along a line transverse to said internal diameter to compress the sleeve (29,61,82) deflects the sleeve portions carrying the lugs (46,66,81) outwardly away from the tube portion (39,39,74) to disengage the lugs (46,66,81) from the grooves (44,44,73) thereby permitting axial adjustment of the tracheostomy tube (11) within the collar (14,60,84) and whereby, upon removal of said pressure, the sleeve (29,61,82), due to its inherent resiliency, returns to its undeflected condition with the lugs (46,66,81) in engagement with the grooves (44,44,73).

* * * * *